(12) United States Patent
Peuscher (10) Patent No.: US 8,248,137 B2
(45) Date of Patent: Aug. 21, 2012

(54) APPARATUS FOR PROCESSING SIGNALS (75) Inventor: Jan Hendrik Peuscher, Enschede (NL)

(73) Assignee: Twente Medical Systems International B.V., Oldenzaal (NL)

( * ) Notice: Subject to any disclaimer, the term of this patent is extended or adjusted under 35 U.S.C. 154(b) by 414 days.

(21) Appl. No.: 12/671,874

(22) PCT Filed: Aug. 4, 2008

(86) PCT No.: PCT/NL2008/050533
§ 371 (c)(1),
(2), (4) Date: Feb. 24, 2010

(87) PCT Pub. No.: WO2009/017413
PCT Pub. Date: Feb. 5, 2009

(65) Prior Publication Data
US 2011/0227638 A1    Sep. 22, 2011

(30) Foreign Application Priority Data
Aug. 2, 2007   (NL) .................................... 1034223

(51) Int. Cl.
*H03K 3/00*   (2006.01)
*A61B 5/04*   (2006.01)

(52) U.S. Cl. ........ 327/291; 327/298; 600/509; 600/546; 600/547

(58) Field of Classification Search .............. 327/77–78, 327/80, 82, 291, 293–295, 298; 600/509, 600/512, 513, 546–547
See application file for complete search history.

(56) References Cited

U.S. PATENT DOCUMENTS

| 4,530,365 A | 7/1985 | Harada et al. |
| 5,513,649 A | 5/1996 | Gevins et al. |
| 5,615,687 A | 4/1997 | Pritchard |
| 5,704,351 A * | 1/1998 | Mortara et al. ............... 600/382 |
| 7,881,778 B2 * | 2/2011 | Rantala .......................... 600/509 |

FOREIGN PATENT DOCUMENTS

| DE | 29 26 165 A1 | 1/1980 |
| EP | 1 554 975 A | 7/2005 |
| JP | 05 220121 A | 8/1993 |

OTHER PUBLICATIONS

Van Eykern et al., *A new technique for simultaneously recording EMG and movements in experimental animals*, Brain Research Protocols, 6:108-118 (2001).
International Search Report dated Dec. 10, 2008 for PCT/NL2008/050533.

* cited by examiner

*Primary Examiner* — An Luu
(74) *Attorney, Agent, or Firm* — Leydig, Voit & Mayer, Ltd.

(57) ABSTRACT

An apparatus for processing signals, in particular physiological measuring signals, wherein the apparatus is provided with different channels with signal inputs (1) for receiving input signals, which input signals each comprise a specific signal component and a signal component common to all input signals, wherein each channel is provided with an impedance transforming input amplifier (3), wherein the apparatus is configured for supplying to the non-inverting input of each input amplifier (3) a respective input signal and, to the inverting input an analogue reference signal common to all channels, wherein the apparatus is provided with a digital signal processor (10) and one more or analogue-digital converters (5) for supplying the signals provided by the input amplifiers (3) to the digital signal processor (10), wherein the signal processor (10) is designed for converting the signals received from the one or more analogue digital converters (5) into one or more output signals.

18 Claims, 5 Drawing Sheets

APPARATUS FOR PROCESSING SIGNALS

FIELD OF THE INVENTION

The invention relates to an apparatus for processing signals, in particular physiological measuring signals, for instance EEG-signals (electroencephalogram signals), wherein the apparatus is provided with several channels with signal inputs for receiving input signals, which input signals each comprise a specific signal component and a signal component common to all input signals, wherein each channel is provided with an impedance transforming input amplifier, wherein the apparatus is configured for supplying to the non-inverting input of each input amplifier a respective input signal and to the inverting input an analogue reference signal which is equal for all channels.

BACKGROUND

Figure 1:
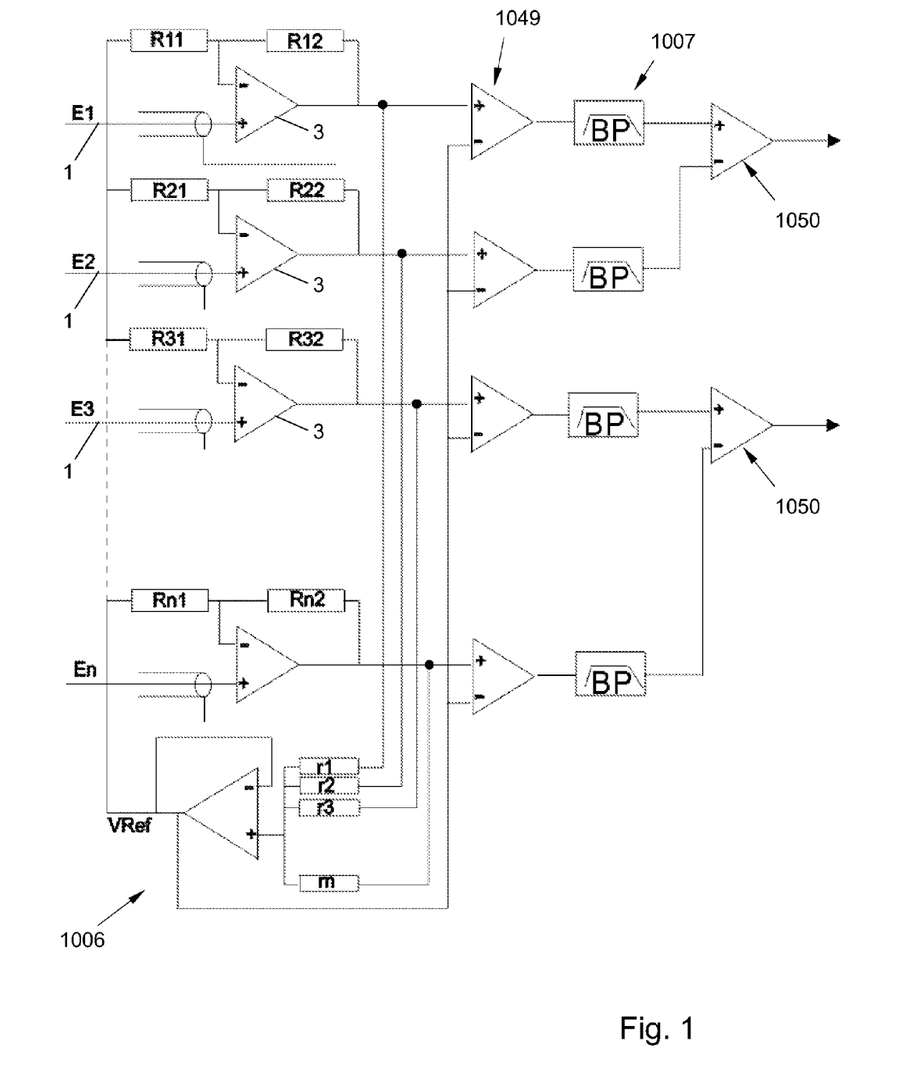
FIG. 1 shows an apparatus known from the state of the art.

Such an apparatus is known from Dutch patent NL187945. An example of such an apparatus is represented in FIG. 1. FIG. 1 shows in particular a reference amplifier known per se which is provided with the several channels with signal inputs 1 for receiving input signals E1, E2, E3, . . . , En. The input signals come in particular from sensor electrodes (not represented in FIG. 1). The input signals can each comprise a specific signal component as well as a signal component common to all input signals. Each channel is provided with an impedance transforming input amplifier 3. The apparatus is configured for supplying to the non-inverting input (in the drawing each time provided with the "+" mark) of each amplifier 3 a respective input signal and to the inverting input (in the drawing each time provided with the "−" mark) an analogue reference signal Vref which is equal for all channels, for providing an associated signal via an output of the input amplifier 3. The known apparatus is further provided with an analogue averager 1006 for forming the reference signal Vref. Further, a second amplifier stage 1049 is provided (see FIG. 1) for removing the common signal component from the signals. Furthermore, one or more differential amplifiers 1050 are provided, in particular for each time further amplifying two associated signals coming from the second stage 1049 in the case of a bipolar input signal measurement. For a further discussion of various components of such an apparatus and particular advantages of the known apparatus, reference is made to the content of NL187945.

It is furthermore known, with the known system, to further provide each channel with a band pass filter 1007 of which an input is coupled to the output of the second amplifier stage 1049. Each band pass filter 1007, which is typically used in the known apparatus, comprises a low pass filter part and a high pass filter part for allowing passage of a particular frequency band BP, which band B, in particular, does not contain DC components.

It has appeared that with particular measurements, for instance electrophysiological measurements, the input signals E1, E2, E3, . . . , En, can each contain various components. A first component in each signal comprises, in particular, the electrophysiological information. A second component comprises, in particular, a mains interference signal. A third component comprises a sensor offset signal (in particular an electrode offset signal).

The electrophysiological information mentioned is in particular the important measurement part of the input signal and can have an amplitude in the range of, for instance, some microvolts to some millivolts.

Mains interference, in particular resulting from 50 Hz or 60 HZ mains AC voltage, is also called a "common mode disturbance". The amplitude of this interference can vary strongly, between, for instance, 1 and 100 mV. As a rule, the reference amplifier system represented in FIG. 1 can quite well remove this interference component from the signals, as the mains interference component will form an important part of the reference signal.

A sensor-offset signal, in particular an electrode offset (the third component in an input signal) can have varying amplitudes, and is generally not stable. It can comprise a DC signal with an amplitude between 0 V and some hundreds of mVs, and can vary with a very low frequency. During use of the apparatus represented in FIG. 1, an average of these offsets also forms part of the reference signal mentioned. Here, the variance in the different offsets of the different inputs signals E1, E2, E3, . . . , En is amplified by the apparatus as if this variance were part of the electrophysiological information signal component. The mutual variance in the offsets can be relatively large, which means that the gain in the first amplifier stage (comprising the input amplifiers 3) of the apparatus shown in FIG. 1 is to be limited. If a said offset variance is for instance 150 mV, the gain is for instance only, at most, a gain 20.

The high pass filter part of the apparatus is intended for removing the offset from the signal, both a non-amplified average offset and an amplified offset variance. As a result, it is possible to have the second amplifier stage amplify the remaining signal once again, for instance 100 times. A physiological signal can have an amplitude of, for instance, 0.1 mV, while the offset variance can already be 150 mV. The offset itself can be as much as 500 mV. To this end, each high pass filter may have a relatively low cut-off frequency of 0.01 Hz, so that it is substantially avoided that DC signals can reach the differential amplifier stage.

A drawback of the known apparatus is that it feeds back an average sensor offset per channel, wherein variances in offset per channel determine how high the amplification can be chosen. When using different sensor-electrode materials, and/or if electrodes make poor contact, the apparatus can attain a saturation mode.

For instance, an artefact in one input signal, for instance a movement artefact or an artefact resulting from a stimulus, can form a relatively large offset in this signal, for instance an offset of a few hundreds mV. This means that the first and second amplifier stages (3, 1049) are saturated. The input amplifier stage 3 and second stage 1049 can leave this saturated mode relatively rapidly, generally within some milliseconds. It has however appeared that the amplifier stage 1050 (which can amplify for instance 100×) can remain out of range for several minutes so that a measurement, comprising the signal processing to be carried out by the apparatus, remains blocked for an undesirably long period of time.

SUMMARY OF THE INVENTION

The present invention contemplates obviating these problems while maintaining the advantages of the apparatus. In particular, the invention contemplates an apparatus for processing signals, in particular physiological measuring signals, which can suitably prevent transmission of particular common signal components, and preferably such that a low frequent signal offset in an input signal needs hardly, if at all, lead to saturation of the amplifier parts of the apparatus.

To this end, the apparatus according to the invention is characterized in that the apparatus is provided with a digital signal processor and one or more analogue-digital converters for supplying the signals, provided by a respective input amplifier, to the digital signal processor, wherein the signal processor is designed to convert signals received from the one or more analogue-digital converters into one or more output signals.

In this manner, in particular a DC reference amplifier can be obtained, with a relatively high dynamic range. Further, in this manner, use of the above-described analogue high pass filters can be omitted. As a result, undesired effects of artefacts in input signals, for instance saturation of an amplifier part of the apparatus for a particular period of time, can be suitably avoided.

The apparatus according to the present invention is in particular designed to indeed allow the passage of DC components, at least to the analogue-digital converter(s), in order that such DC components can be detected in a downstream part of the apparatus, or for instance by the digital signal processor of the apparatus, or by a further signal processor coupled to the apparatus, and can for instance be digitally removed from the signal stream.

According to a further elaboration of the invention, each channel is provided with a low pass filter, of which one entrance is located signal-downstream with respect to a respective input amplifier, and of which the output is located signal-upstream with respect to this analogue-digital converter. As mentioned, the apparatus is preferably not provided with a high pass filter, at least not in each channel between an input amplifier and the analogue-digital converter(s) so that any sensor dependent offset signal parts (as described hereinabove) that may be present in a signal can reach a downstream analogue-digital converter. Accordingly, the low pass filter mentioned is designed for indeed allowing the passage of analogue DC signal components.

In an advantageous embodiment, the apparatus is provided with an averager for forming the reference signal. In that case, it is advantageous when the averager is connected to outputs of the input amplifiers, via connections present signal-upstream with respect to the low pass filters that are preferably also present. It is further favourable if the averager is provided with an impedance transforming amplifier, of which an output is coupled, in particular, to the inverting inputs of the input amplifiers for supplying said reference signal.

According to an advantageous embodiment, the digital signal processor is designed for processing, in particular digitally averaging, the signals received from the one or more analogue-digital converters, for supplying a digital reference signal, wherein the apparatus is provided with a digital-analogue converter for converting the digital reference signal into the analogue reference signal.

Further, each channel is preferably provided with a compensation amplifier of which a non-inverting input is arranged for receiving the preferably low pass filtered signal from a respective input amplifier, and of which one output is directly or indirectly coupled to an analogue-digital converter, wherein an inverting input of the compensation amplifier is coupled via a digital-analogue converter to the signal processor for receiving a control signal therefrom. In that case, according to a further elaboration, the signal processor can be designed for providing each control signal under the influence of and/or while utilizing one or more signals obtained from the one or more analogue-digital converters, respectively.

In addition, the digital signal processor can for instance be designed for detecting a (low frequency) signal offset voltage for each channel, and for adapting this control signal for removing at least a part of a detected signal offset voltage from the respective signal.

In particular, a detected signal offset potential is removed by digital means from the respective signal. Here, the value of this potential becomes known and can be used as additional information of the digital signal information, so that the resolution of the analogue-digital conversion can be limited. Here, a high pass can be digitally simulated, in particular under software control by the digital signal processor, in particular to prevent a signal-downstream amplifier stage (1050) from jamming. This signal can further be used for reconstructing the original DC signal.

Furthermore, in this manner, use of an analogue high pass filter can be avoided and use can still be made of the advantages of an additional amplifier stage, for amplifying the physiological signal, and an associated lower resolution of the analogue-digital conversion. These analogue-digital converters are also much faster, less expensive and consume less power than A/D converters with high resolutions. All this is for instance advantageous when developing battery-fed and ambulant measuring equipment.

According to an especially advantageous elaboration of the invention, the apparatus is provided with a multiplexer and one analogue-digital converter. The multiplexer can supply the signals coming from the channels mentioned to the analogue-digital converter. The multiplexer may comprise a random driven multiplexer, for instance a multiplexer which supplies the signals coming from the channels mentioned to the analogue digital converter not in a predetermined order but in random order. However, all this is preferably such that the multiplexer supplies the signals coming from the channels mentioned to the analogue digital converter in a predetermined order. According to a further elaboration, inputs of the multiplexer can be coupled to outputs of the different compensation amplifiers, if present. Further, the multiplexer can modify a predetermined order for a number of N different channels preferably periodically, and more preferably each time all N channels have been "addressed", wherein the order mentioned preferably comprises an alternating increasing and decreasing order, from a first to a last channel and vice versa.

The invention further provides software which is provided with a program code executable by a computer or processor, which program code is designed for having a computer or compressor function as a signal processor of an apparatus according to the invention when the code executed by the compressor or processor, respectively.

BRIEF DESCRIPTION OF THE DRAWINGS

The invention will presently be elucidated in further detail on the basis of the Figures, in which.

In this application, identical or corresponding features are indicated with identical or corresponding reference numerals.

DETAILED DESCRIPTION OF THE DRAWINGS

As described hereinabove, FIG. 1 shows an example of a known reference amplifier. In the following, various apparatuses are described, which offer various advantages over the system represented in FIG. 1.

Figure 2:
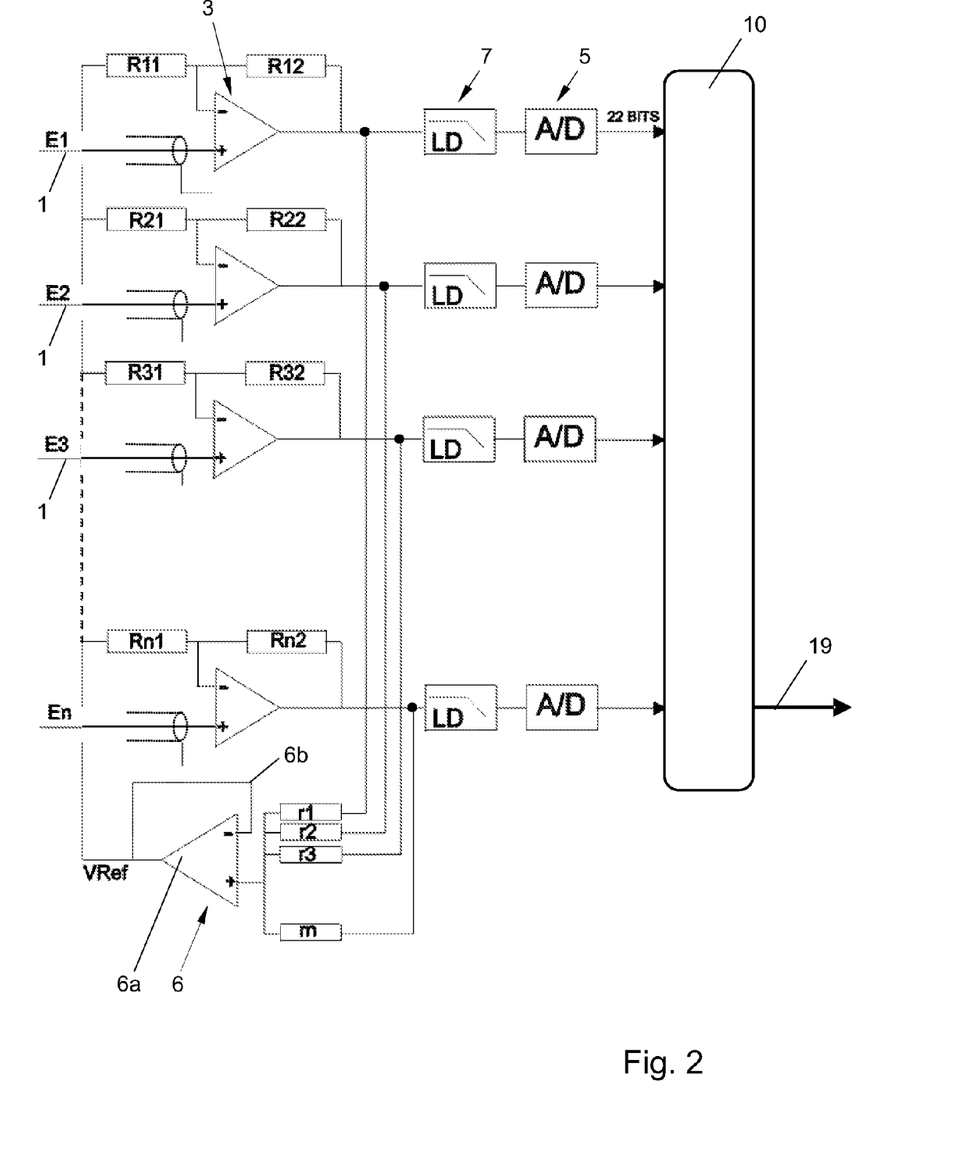
FIG. 2 shows a first exemplary embodiment of the present invention.

FIG. 2 shows a modified apparatus, comprising, in particular, a DC reference amplifier. The apparatus represented in FIG. 2, which serves for processing signals, in particular physiological measuring signals supplied through sensors (not represented), is provided with several (N) channels with N signal inputs 1 for receiving input signals, which input signals E1, E2, E3, . . . , En (with n being 1, 2, 3, . . . , N) each comprise a specific signal component and a signal component common to all input signals. Furthermore, for a particular period of time, one or more input signals E1, E2, E3, . . . , En can contain sensor related offset signal parts, as is described hereinabove.

Preferably, the different channels (also called signal paths) can be designed in the same manner. Each channel is preferably provided with an impedance transforming input amplifier 3. These amplifiers 3 are preferably operational amplifiers (Opamps). The present apparatus is configured for supplying to the non-inverting input of each input amplifier 3 a respective input signal E1, E2, E3, . . . , En and, to the inverting input, an analogue reference signal Vref common to all channels, for providing an associated amplifier output signal via an output of the input amplifier 3. To this end, in FIG. 2, the apparatus is provided with an analogue averager 6 which is designed for forming the reference signal. In particular, the inverting input of each input amplifier is communicatively coupled, by means of a first respective impedance R11, R21, R31, . . . , Rn1 to an output of the averager, for receiving the reference signal Vref. Furthermore, by means of a second respective impedance R12, R22, R32, . . . , Rn2, the inverting input of each input amplifier 3 is brought into signal connection with the output of this amplifier. In particular, the first impedances R11, R21, R31, . . . , Rn1, are resistances wherein, according to a relatively simple design, all resistances R11, R21, R31, . . . , Rn are preferably identical. The same holds for the second impedances R12, R22, R32, . . . , Rn2. As will be clear to the skilled person, the gain supplied by each input amplifier 3 is set by the ratio between the respective first and second resistance.

In an advantageous manner, the apparatus is provided with a digital signal processor 10, and several analogue-digital converters (A/D converters) 5, i.e. one per channel, for supplying the amplified signals provided by the input amplifiers 3, to the digital signal processor 10.

The signal processor 10 is designed for converting signals received from the one or more analogue-digital converters 5 into at least one or more output signals, and outputting this/these, for instance, via a signal output 19. The signal output 19 can be designed in different manners, and for instance comprise a digital output, in particular a serial output, and can for instance be suitable for supplying output signals relating to a large number of channels (for instance 128 channels, or another number). An output signal supplied by signal processor 10 can for instance comprise a digital signal stream, which is provided with the digital signals coming from the different channels, for instance in a predetermined order. Alternatively, the signal processor 10 may be designed for parallel outputting of the digital signals coming from the different channels via a parallel signal output (not represented).

The exemplary embodiment according to FIG. 2 is further provided with low pass filters 7. In particular, each channel is provided with such a low pass filter 7, which allows for instance passage of signal parts LD with frequencies from 0 Hz up to a particular cut-off frequency, and substantially prevents passage of signal parts with frequencies higher than the cut-off frequency. Such cut-off frequency can in particular be such that the generally known Nyquist criterion is met with respect to the frequencies of the signals to be detected, which will be clear to the skilled person.

An input of each filter 7 is for instance directly or indirectly coupled to the output of a respective input amplifier 3, of the same channel, for receiving the signal coming from this amplifier. The output of each filter 7 is each time in particular upstream with respect to a respective analogue-digital converter 5. The different channels of the apparatus themselves are not provided with high pass filters, this contrary to the apparatus represented in FIG. 1. In this manner, the adverse effects of a sustained saturation resulting from the time constant of such a high pass filter are avoided.

With the exemplary embodiment of FIG. 2, the analogue averager 6 is communicatively connected to outputs of the input amplifiers 3, via signal connections which are located signal-upstream with respect to the low pass filters 7. The analogue averager 6 is provided with an impedance transforming amplifier 6a (preferably an Opamp), of which an output is coupled in particular to the inverting inputs of the input amplifiers 3, via said first impedances R11, . . . , Rn1 for supplying said reference signal Vref to the input amplifiers 3. The present averager 6 is provided in a simple manner with a series of parallel arranged third impedances, in particular third resistances r1, r2, r3, . . . , m which are preferably identical to each other, and which couple the outputs of the input amplifiers 3 to the non-inverting input of the averaging amplifier 6a. It is preferred that the inverting input and output of the amplifier 6a of the averager are directly coupled, via a signal connection 6b. In other words: the amplifier 6a is provided in an input-follower configuration, and thus provides for a gain 1× with a high input impedance and low output impedance, which configuration is generally known per se.

Preferably, each of the A/D converts 5 has a high dynamic range. To this end, use can for instance be made of A/D converters of a resolution of 20 bits or higher, for instance a resolution of 21 or 22 bits, or a different resolution. Example: suppose that an analogue-digital range is approximately ±3 Volts and the LSB (least significant bit) resolution is 1 microvolt, the number of bits of the A/D converter 5 should then be at least 22 bits (21 bits is sufficient for 3 Volt; therefore, for +3 and −3 Volt, the resolution should be 22 bits, the 'sign bit' included), which will be clear to the skilled person. If the input stage of the apparatus (comprising the input amplifiers 3) is for instance configured for supplying a gain of 20×, an A/D converter resolution of 0.07 microvolts LSB follows.

The signal processor 10 can comprise, for instance, a digital signal processor (DSP), and can be provided by hardware, software or a combination thereof. The signal processor 10 itself can be designed for processing digital signals received from the A/D converters 5 such that certain sensor related offsets in those signals are substantially removed from the signals. To this end, the signal processor 10 can for instance be designed for detecting such offsets. Here, processing of the data is preferably such that a detection and modification of a digital signal part coming from one of the channels mentioned has no influence on the digital signal parts coming from the other channels.

Optionally, the signal processor 10 can be designed for carrying out a high pass filtering of each of the digital signals received from the A/D converters while utilizing, for instance, one or more suitable high pass filters designed in software.

In an advantageous embodiment, the signal processor 10 is only designed to receive the digital data streams received from the A/D converts 5 and convert these into one digital output signal stream, wherein the signal processor 10 utilizes no digital signal offset compensation and carries out high pass filtering. The output signal stream can for instance be processed further by a data processor (for instance computer, not represented) and/or can be saved. Such a data processor can for instance comprise suitable hardware and/or software, which is designed for detecting signal offsets in the output signal steam, per channel, and for removing the detected offsets for each channel. The data processor (not represented) can for instance be designed for carrying out a high pass filtering of the digital channel parts received from the signal processor 10.

In the present exemplary embodiment, it is further advantageous when a data processor is designed for digitally detecting the signal component common to all input signals. Then, the data processor can process the received signals for removing a detected common signal component from the signals. Thus, with additional advantage, the data processor can take over the function of analogue signal compensation means 1049 (see FIG. 1), per channel.

The advantage of the apparatus represented in FIG. 2 is that amplification of input signals needs only be supplied by one amplifier stage (comprising the reference input amplifiers 3). Furthermore, the complete amplifier stage is DC-coupled. Subsequently filtering and compensating the digitized signals can simply be carried out by suitable digital hardware and/or software (preferably by a data processor, not represented).

Figure 3:
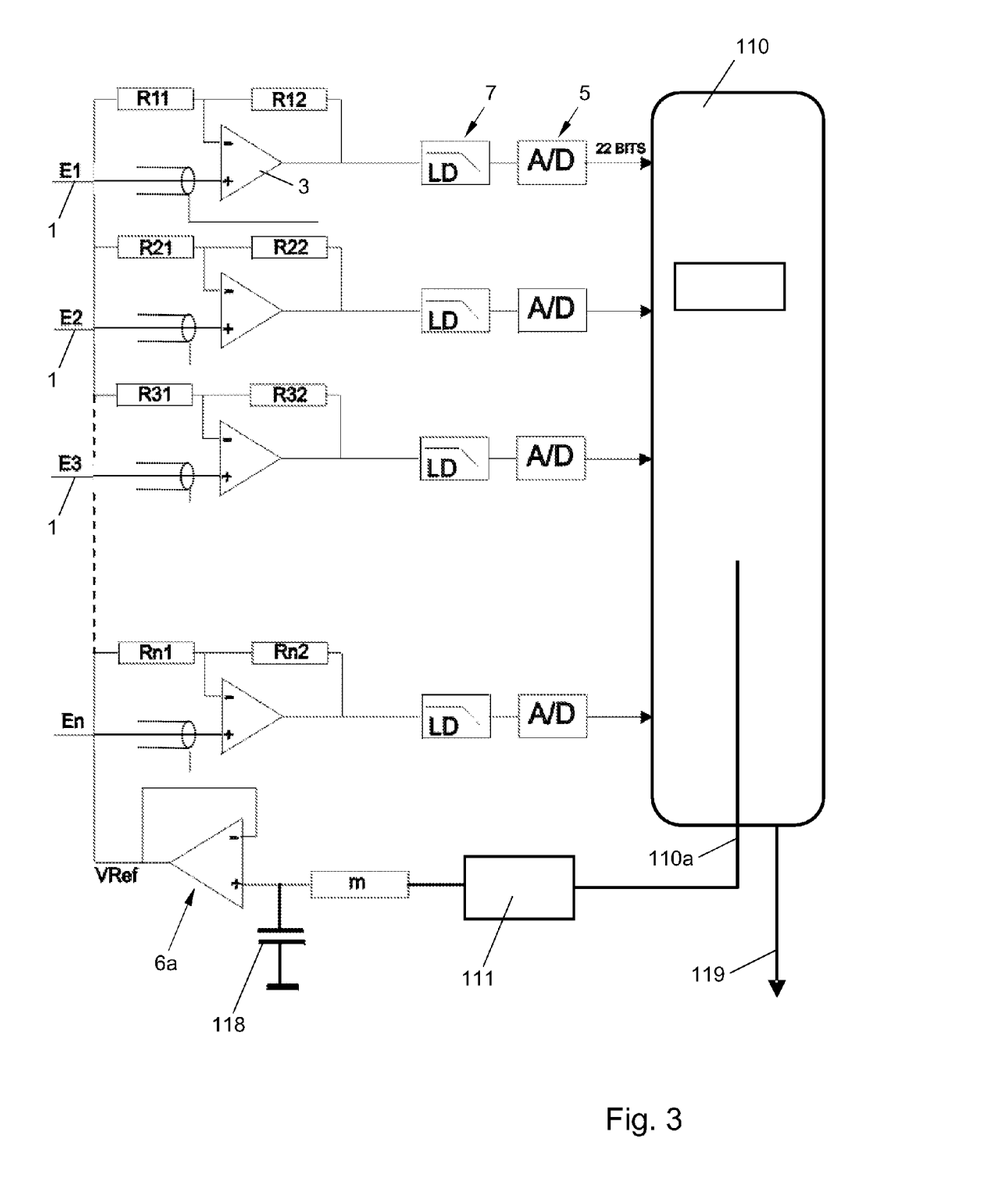
FIG. 3 shows a second exemplary embodiment of the present invention.

FIG. 3 shows an advantageous exemplary embodiment of the invention, which is distinguished from the elaboration represented in FIG. 2 in that the signal processor 101 is designed for supplying a digital reference signal, which digital reference signal is converted into said analogue reference signal Vref by suitable converter means 111, 6a. The apparatus according to FIG. 3 is in particular no longer provided with an analogue averaging system, but with a digital signal averager which forms part of the signal processor 110.

In FIG. 3, in particular, the digital signal processor 110 is designed to process, in particular digitally average, the digital signals received from the A/D converters 5, for providing the digital reference signal. Said averaging is schematically represented in FIG. 3 and comprises, for instance, a summation step Σ wherein the digital signals, coming from the N different channels, are added up, and a division step 1/N wherein the sum of the digital signals (i.e. the result of said summation step) is divided by the number N of those signals (i.e. the number of channels). The digital result of this operation comprises a digital reference signal, which is supplied via a signal output 110a to a digital-analogue (D/A) converter (DAC) 111 (for instance a 20 bit D/A converter 111). This D/A converter 111 converts the digital reference signal into an analogue signal, which analogue signal is processed via an impedance transforming amplifier 6a for providing the analogue reference signal Vref. To this end, the output of the D/A converter 111 is coupled via a suitable impedance (in particular comprising a resistance in) to the non-inverting input of this amplifier 6a, while the inverting amplifier input is electrically short-circuited to the amplifier output. In this case, the non-inverting amplifier input is preferably earthed via a condenser 118.

The signal processor 110 is further provided with an output 119 for outputting output signals (see above). Preferably, the signal processing is integrally provided with digital high pass filters, for instance designed in software, for filtering signal components below a particular cut-off frequency from the signals. It will be clear to the skilled person how such a digital high pass filter, as such, can be designed. Preferably, the digital high pass filtering is not carried out before the summation step Σ is carried out, so that, also, an average offset signal becomes part of the reference signal, and the amplification of the input opamps 3 can be based on the variance of the offset signals. Here, a cut-off frequency of each digital high pass filter can for instance be 1 Hz or less, in particular 0.1 Hz or less, more particularly 0.01 Hz or less, in particular for substantially removing DC components from the digital signals.

A great advantage of the apparatus represented in FIG. 3 is that it comprises a digital DC reference amplifier, provided with digital components for calculating the reference signal. The calculation (comprising, for instance, the summation step Σ and division step 1/N) of the digital reference voltage can for instance be carried out by suitable software of the signal processor 110. A further advantage is that this calculation is carried out digitally and therefore no longer depends on analogue components (such as the various resistances r1, r2, . . . , rn of the exemplary embodiment represented in FIG. 2). In a further elaboration, the signal processor 110, such as in the exemplary embodiment represented in FIG. 2, can process the signals such that specific sensor related offsets are removed from the signals, per channel.

Figure 4:
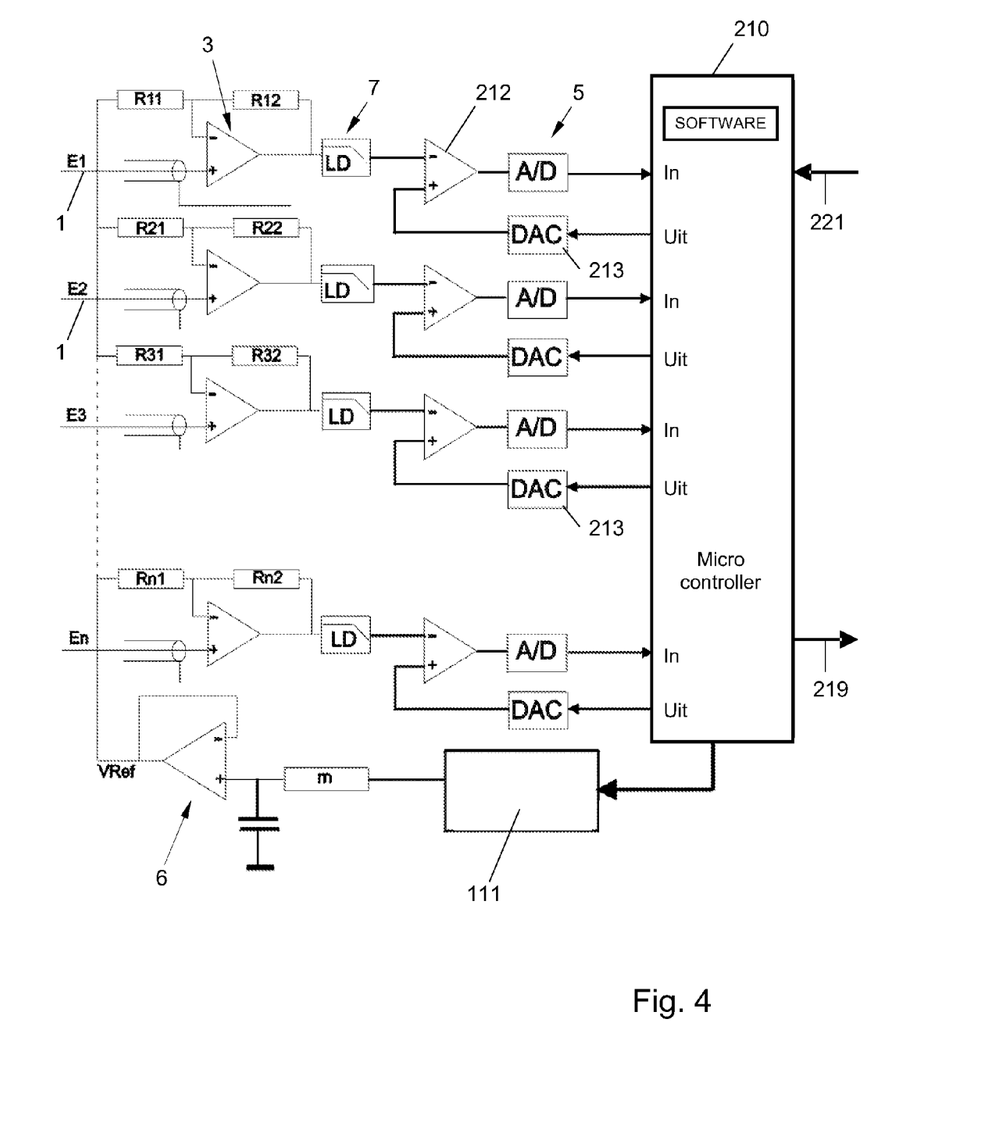
FIG. 4 shows a third exemplary embodiment of the present invention.

FIG. 4 shows an especially advantageous elaboration of the invention, comprising a compensated digital DC reference amplifier. The elaboration according to FIG. 4 is distinguished from the exemplary embodiment according to FIG. 3 in that a second amplifier stage is provided, comprising compensation amplifiers (in particular Opamps) 212 which are each arranged in a respective channel between a low pass filter 7 and A/D converter 5. In particular, the non-inverting input of each compensation amplifier 212 is arranged for receiving the low pass filtered amplified signal from a respective input amplifier 3, via a filter 7. In the present exemplary embodiment, an output of each compensation amplifier is directly coupled to an A/D converter 5 for providing a signal compensated by the amplifier 212 to the A/D converter 5, wherein the A/D converter supplies the digitized signal to a respective input (In) of the signal processor 210. Alternatively, a low pass filter 7 is arranged in a channel between the compensation amplifier 212 and respective A/D converter 5 (in that case, the input of this filter 7 is still located signal-downstream with respect to the respective input amplifier 3).

In an advantageous manner, the inverting input of each compensation amplifier 212 is coupled via a suitable digital-analogue converter 213 to a respective output (Out) of the signal processor 210 for receiving a control signal therefrom. In this case, the signal processor 210 comprises, for instance, a microcontroller, with suitable software for carrying out various signal processing functions of the signal processor 210. These signal processing functions comprise, in particular: calculating a digital reference signal, producing suitable control signals to be supplied to the D/A converters 213 and providing output signals, via the (preferably serial) output 219.

The signal processor 210 can further be provided with, for instance, one or more other inputs, for instance a serial input 221 for communication with other modules or components. According to a further elaboration, the input 221 can communicate with, for instance, other modules, so that improved modularity and synchronisation with respect to other signal systems, and the flexibility with regard to extension of the number and types of channels can be obtained.

According to a further elaboration, the signal processor 210 is designed for providing each control Signal under the influence of and/or while utilizing one or more digital signals obtained from the analogue digital converters 5.

Preferably, the signal processor 210 is designed for detecting a signal offset voltage for each channel (at least, a channel-specific offset, for instance a electrode offset mentioned), and for adapting the control signal such that the respective compensation amplifier 212 can remove at least a part of the signal offset-voltage from the signal under the influence of this control signal—supplied via the D/A converter 213 to this amplifier 212.

In particular, from each channel an average offset potential and amplified offset variance is then compensated so that the respective compensation amplifier 212 only amplifies the physiological component and a part of the common component, this being the common part not belonging to the low frequent offset. Even the use of different electrode materials is thus an option.

If the signal processor 21 detects, for instance, that in the second channel (with respect to the second input signal E2), during a particular measuring period, a particular low frequent offset voltage variation is present, the signal processor 210 can control the D/A converter via the respective digital output ('out(2)') for supplying the same voltage variation to the inverting input of the respective compensation amplifier 212. Thus, per channel, the offset variance can be rapidly and accurately compensated.

During use, the average offset and the offset variance are preferably completely compensated. In this manner, the average of the offset still present 1× amplified in the signal, and the offset variance can be completely compensated. The signal processor 210 needs not distinguish the offset variance. This very low frequent and fairly high amplitude of the offset signal is for instance digitally known, in processor 210, and can be removed from the signal by means of compensation amplifier 212. As a result, a substantially physiological signal remains. This signal is additionally amplified and digitized. In the signal processor 210, the compensated offset and the digitized physiological component can be joined into one digital signal, if this is required. Owing to the additional amplification, for instance A/D converters 5 with relatively low resolutions can be used.

According to a further elaboration, the signal processor 210 can be arranged to take the specific design of the compensation amplification stage 212 into account for producing an accurate signal offset compensation per channel. The signal processor 210 may be provided with calibration data with respect to linearity and gain of the compensation amplifiers 212, which calibration data are for instance used by the signal processor 210 when determining the control signals. Such calibration data can for instance be saved in a memory (not specifically represented) of the signal processor 210, and for instance be pre-entered or be determined by the signal processor 210 via a suitable calibration step. With such a calibration step, known input signals may be supplied to the inputs 1 of the apparatus. An optional compensation stage calibration can also comprise a different calibration method, which will be clear to the skilled person.

In the exemplary embodiment of FIG. 4 too, it is advantageous when the signal processor 210 is designed to carry out a high pass filtering of each of the digital signals received from the A/D converters 5.

The elaboration according to FIG. 4 has several advantages. For instance, a relatively high gain can be used, for instance 500× (for instance 10× in the input stage 3 and 50× in the compensation stage 212, or a different, suitable proportion), so that A/D converters 5 with a relatively low resolution, low disturbance, high sample frequency and virtually no delay can be used. In this manner (for instance physiological) measuring signals can be distinguished from other signal parts particularly well and be detected. In particular, offset per channel can be compensated well, so that the amplification per channel no longer depends on the offset variances, but only on the electrophysiological signal characteristics (i.e. the specific signal components mentioned). Furthermore, the capacity to remove common signal components from the signals can thus be improved considerably, while power consumption can decrease.

Figure 5:
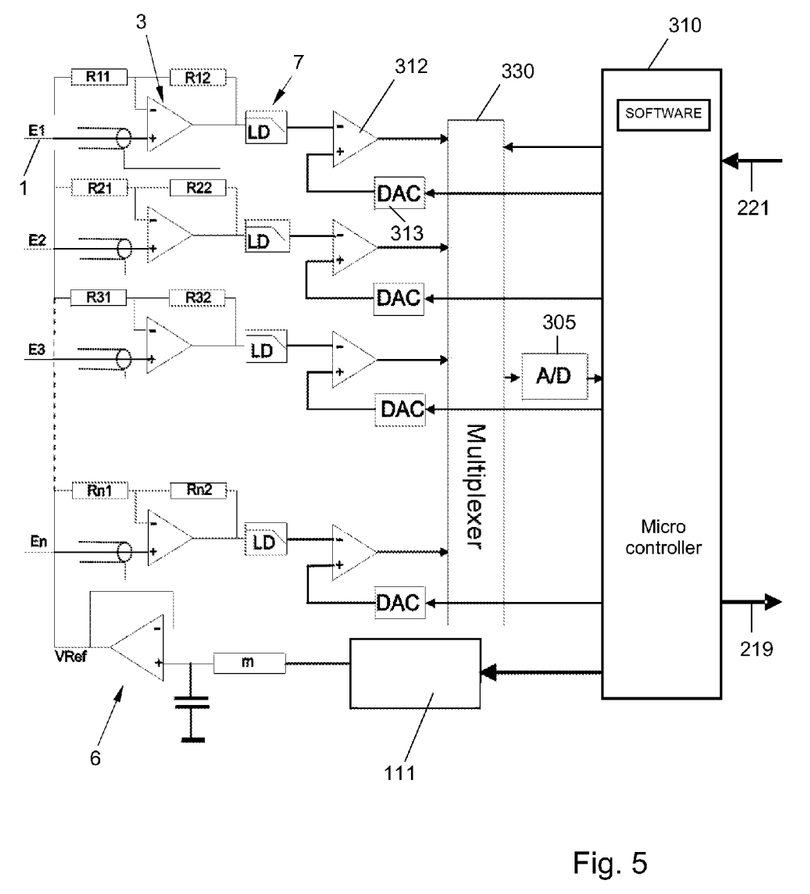
FIG. 5 shows a fourth exemplary embodiment of the present invention.

FIG. 5 shows a further advantageous elaboration of the invention, which is based in particular on the elaboration according to FIG. 4. Here, (in the system of FIG. 5) use of the compensation stage is not required, but it is advantageous.

As shown in FIG. 5, it is advantageous when the apparatus is provided with a multiplexer 330 and only one analogue-digital converter 305, wherein the arrangement is set up such, at least coupled to each other such that the multiplexer 330 supplies the amplified signals coming from the various channels in a predetermined order to the analogue digital converter 305. The A/D converter supplies the successively digitized signals to the signal processor 310. In this case, the compensation amplifiers 312 are therefore indirectly coupled to the A/D converter 305. In the present exemplary embodiment, the inputs of the multiplexer 330 are coupled to outputs of the several compensation amplifiers 312; in an alternative elaboration, the multiplexer inputs may be directly coupled to outputs of the low pass filters 7. Further, once again, preferably D/A converters 313 are provided, for transmitting control signals from the signal processor 310 to the compensation amplifiers 312.

According to an especially advantageous elaboration, the multiplexer 330 is designed to, during use, periodically alter the predetermined order for the N different channels. Preferably, the alteration takes place each time all N channels have been "addressed" once (at least, each time the signal of each of the N channels has been transmitted once by the multiplexer 330 to the A/D converter 305), while the order preferably comprises an alternately increasing and decreasing order, from a first channel (n=1) to last channel (n=N) and vice versa. In the latter case, the order of the channels of which the multiplexer 330 transmits the signal to the A/D converter 305 is, for instance, in the channel order (for channels 1, 2, . . . , N): n=1, n=2, . . . , n=N−1), n=N, n=N, n=(N−1), n=(N−2), . . . , n=2, n=1, n=1, n=2, . . . , n=(N−1), n+N, n=N, n=(N−1), n=(N−2), . . . , n=1, etc. Another order, other than an each time the same order for a number of N channels, is possible too.

In this manner, a simpler and more compact system can be obtained, with fewer components, which furthermore consumes less power. Through the use of the repeatedly altering multiplexer signal transmission order, multiplexer related phase problems, which could in particular arise when using the optional compensation amplification stage if such an order is not utilized, can be avoided.

The present invention can offer various advantages, as has already been described hereinabove. The invention can in particular present an apparatus wherein different signals can be processed via different channels, for amplifying specific signal components, for the purpose of detection, and, in particular, for distinguishing the specific components of common signal components (separation of specific signal components and common components can be carried out by the apparatus itself, or, for instance, by digital signal processing means arranged downstream). Here, in particular, a relatively high gain can be utilized on the input signals by an amplifier stage 3 located signal-upstream, for instance a gain of 50× or more, in particular 100× or more, or another value.

Here, in particular a digital circuit, at least a digital signal processor 10, 110, 210, 310 is integrated into the apparatus. The apparatus is preferably designed such that DC components typically present in the input signals (for instance DC offset parts) can reach the digital signal processor via respective channels, wherein the channels are preferably not provided with DC filtering means.

A common signal component can for instance be digitally calculated from digital information. Preferably, a feedback loop 111, 6 is available for feeding a digitally calculated common signal component as reference signal back to the reference amplifier part 3 of the apparatus.

More preferably, furthermore, a specific offset per channel is calculated by the digital signal processor (for instance by suitable software of the digital signal processor) while utilizing the signals digitized by the A/D converter(s) 5, 305, such as, for instance, in the elaboration according to FIG. 4 or FIG. 5. The thus calculated specific offset can then simply be compensated, per channel, via said compensation amplifier stage 212, 312.

In any case, removing a signal component (in particular a mains component, for instance a 50 Hz or 60 Hz AC component) common to all input signals from the analogue input signals is preferably completely controlled by/via the digital signal processor 110, 210, 310, while utilizing the signals digitized by the A/D converter(s) 5, 305. This is, however, not essential, see the elaboration according to FIG. 2.

It is self-evident that the invention is not limited to the exemplary embodiments described. Various modifications are possible within the framework of the invention as set forth in the following claims.

The invention claimed is:

1. A reference amplifier apparatus for processing signals, in particular physiological measuring signals, the apparatus comprises:
    multiple channels with signal inputs for receiving input signals, the input signals each comprising a specific signal component and a signal component common to all input signals, wherein each channel comprises an impedance transforming input amplifier,
    wherein the apparatus is configured for supplying to each input amplifier a respective input signal and, an analog reference signal which is equal for all channels,
    wherein the apparatus further comprises a digital signal processor and one or more analog-digital converters for supplying the signals provided by the input amplifiers to the digital signal processor, wherein the digital signal processor is designed for converting signals received from the one or more analog-digital converters at least into one or more output signals, wherein said signal processor is designed for processing the signals received from the one or more analog-digital converters, for providing a digital reference signal, wherein the apparatus comprises a digital-analog converter for converting the digital reference signal into said analog reference signal.

2. An apparatus according to claim 1, wherein each channel comprises a low pass filter of which an input is located signal-downstream with respect to a respective input amplifier, and of which the output is located signal-upstream with respect to said analog-digital converters.

3. An apparatus according to claim 2, wherein the apparatus comprises an averager for forming the reference signal, and wherein said averager is connected to outputs of the input amplifiers, via connections which are located signal upstream with respect to the low pass filters.

4. An apparatus according to claim 1, wherein the apparatus comprises an averager for forming the reference signal.

5. An apparatus according to claim 1, wherein said signal processor is designed for digitally averaging the signals received from the one or more analog-digital converters, for providing the digital reference signal, wherein the apparatus comprises a digital-analog converter for converting the digital reference signal into said analog reference signal.

6. An apparatus according to claim 1, wherein each channel comprises a compensation amplifier of which an input is arranged for receiving the preferably low pass filtered signal of a respective input amplifier, and of which an output is directly or indirectly coupled to a said analog-digital converter.

7. An apparatus according to claim 6, wherein an input of the compensation amplifier is coupled via a digital analog converter to said signal processor for receiving a control signal therefrom.

8. An apparatus according to claim 6, wherein the signal processor is designed for supplying each said control signal under the influence of and/or while utilizing one or more signals obtained from the, or one or more, analog-digital converters, respectively.

9. An apparatus according to claim 7, wherein the signal processor is designed for detecting a signal offset voltage for each channel, and for adapting said control signal for removing at least a part of a detected signal offset voltage from a signal coming from a respective input amplifier.

10. An apparatus according to claim 9, further comprising an arrangement including a multiplexer and one analog-digital converter, the arrangement being such that the multiplexer supplies the signals coming from said channels in a predetermined order to the one analog-digital converter.

11. An apparatus according to claim 10, wherein inputs of the multiplexer are coupled to outputs of the compensation amplifiers for the channels.

12. An apparatus according to claim 11, wherein the multiplexer periodically alters the predetermined order for a number of N different channels, each time all N channels have been "addressed".

13. An apparatus according to claim 10, wherein the multiplexer periodically alters the predetermined order for a number of N different channels each time all N channels have been addressed, wherein said order comprises alternately an increasing and a decreasing order, from a first to a last channel and vice versa.

14. An apparatus according to claim 13 wherein said order comprises alternately an increasing and a decreasing order, from a first to a last channel and vice versa.

15. An apparatus according to claim 10, wherein the multiplexer periodically alters the predetermined order for a number of N different channels, each time all N channels have been "addressed".

16. Use of an apparatus according to claim 1 for processing physiological measuring signals supplied by sensors.

17. A non-transient computer-readable medium including program code executable by a computer or processor, the program code being designed for having a computer or processor function as a signal processor of an apparatus according to claim 1 when the code is executed by the computer or processor.

18. An apparatus according to claim 16 wherein said order comprises alternately an increasing and a decreasing order, from a first to a last channel and vice versa.

* * * * *